(12) United States Patent
Chang

(10) Patent No.: US 7,090,493 B2
(45) Date of Patent: Aug. 15, 2006

(54) DENTAL IMPLANT SYSTEM

(76) Inventor: Sang-Kohn Chang, Daegu (KR)

( * ) Notice: Subject to any disclaimer, the term of this patent is extended or adjusted under 35 U.S.C. 154(b) by 0 days.

(21) Appl. No.: 10/500,443

(22) PCT Filed: Jan. 14, 2003

(86) PCT No.: PCT/KR03/00068

§ 371 (c)(1),
(2), (4) Date: Dec. 20, 2004

(87) PCT Pub. No.: WO03/059188

PCT Pub. Date: Jul. 24, 2003

(65) Prior Publication Data

US 2005/0100863 A1 May 12, 2005

(30) Foreign Application Priority Data

Jan. 15, 2002 (KR) ............. 10-2002-0002286

(51) Int. Cl.
*A61C 8/00* (2006.01)
(52) U.S. Cl. ........................... 433/173
(58) Field of Classification Search ............ 433/173, 433/174, 175
See application file for complete search history.

(56) References Cited

U.S. PATENT DOCUMENTS 4,486,178 A 12/1984 Schulte
4,547,157 A * 10/1985 Driskell ............... 433/173
4,758,160 A * 7/1988 Ismail ................. 433/173
4,768,956 A * 9/1988 Kurpis ................. 433/173
5,007,835 A 4/1991 Valen
5,009,596 A * 4/1991 Soderberg ............ 433/173
5,209,666 A * 5/1993 Balfour et al. ........ 433/173
5,312,255 A 5/1994 Bauer
6,290,500 B1 * 9/2001 Morgan et al. ........ 433/173

FOREIGN PATENT DOCUMENTS

JP 54-156389 12/1979

* cited by examiner

*Primary Examiner*—Ralph A. Lewis
(74) *Attorney, Agent, or Firm*—Fish & Richardson P.C.

(57) ABSTRACT

The present invention relates to an implant system for teeth, and in particular to an improved implant system for teeth which is capable of enhancing strength of an implant tooth by improving an assembling structure of an implant planted in an alveolar bone, an abutment assembled to the implant and a crown covering the surface of the abutment, and implementing an easier dental operation, so that it is possible to increase a selectable range of operation based on the condition of patient's teeth.

5 Claims, 7 Drawing Sheets

DENTAL IMPLANT SYSTEM

BACKGROUND OF THE INVENTION

1. Field of the Invention

The present invention relates to a dental implant system, and in particular to an improved dental implant system which is capable of enhancing a strength of a dental implant by improving an assembling structure of an implant root planted in an alveolar bone, an abutment assembled to the implant root and a crown covering the surface of the abutment, and implementing an easier dental operation, so that it is possible to increase a selectable range of operation based on the condition of patient's teeth.

2. Description of Related Art

In the dental implant system, an implant root is inserted into an alveolar bone and is combined to a bone. Thereafter, an abutment adapted to support the implant is engaged to the implant root. A crown is covered onto the abutment. According to the above implant system, it is possible to independently plant one tooth. In addition, since the thusly planted implant has a certain supporting force, it is unnecessary to cut a natural tooth due to the damaged tooth or drawn-out tooth. In other cases, it is possible to stably support a denture. In addition, the life span of the same is long, and a physical appearance of the teeth is good. There are many advantages.

In detail, the implant may be classified into a screw type and a non-screw type.

FIG. 1 is a view illustrating a screw type system which is first introduced and is most widely used and has the U.S. Pat. Nos. 4,330,891, 4,763,788, 4,824,372, 5,064,375, 5,064,425, 5,069,622, 5,080,589, 5,098,293, 5,125,841, 5,145,371, 5,154,612, and 5,269,685.

As shown therein, the screw type implant includes an implant root I which has a self-tapped screw I1 in an outer circumference of the same and is inserted into and combined with an alveolar bone S, an abutment A which is fixed to the implant root I by an abutment screw A1 screwed to an inner circumference of the same, and a crown engagement member E which is engaged to the abutment A by a fixing screw A2 of the crown.

Here, reference character A0 represents an auxiliary screw which seals a screw hole of the implant root I until the implant root I is combined with the alveolar bone S and helps a bone combination of the implant root in the alveolar bone and prevents an insertion of a debris of food. A dotted line represents a crown C processed and installed, after the alveolar bone and the operated portions are healed up.

The above screw type implant system needs lots of parts, so that the fabrication and maintenance costs are expensive, and an operation is complicated. Therefore, a complication may be developed. In addition, the medical care insurance rate of the patient may be increased.

In particular, the above system is implemented based on an engaging force of the screws A1 and A2 between the parts, the maximum external force such as a uniting force, etc. is determined based on the size of the width of the screw thread and the width and length of the implant. Therefore, the supporting force is small. In case that the supporting force is not bearable, the screws may be loosened.

In addition, the dental implant system in the screw type may be resistant to the compressing force when a uniting function is performed in the mouth. However, when the tension force is increased, the screws may be loosened during the use of the implant.

In addition, a certain gap between the implant root and abutment is formed by a poor interconnection between the implant root and abutment, whereby a certain bacteria may invade thereto to cause a sanitation problem and an inflammation in a surrounding tissue, so that an alveolar bone may be absorbed.

FIG. 2 is a view illustrating the dental implant system of the non-screw type which is invented to overcome the problems of the screw type implant system. As shown therein, there is provided a locking taper method which is implemented based on a surface friction force with respect to the engagement between parts.

The constitution of FIG. 2 is a representative in the locking taper method which is commercially available of "Bicon".

In the constitution of the above system, a well I2 having the tapered surfaces which are expanded in an upper direction is formed in the interior of the implant I inserted into the alveolar bone S, and a post portion A3 having a certain taper corresponding thereto is extended in a lower portion of the abutment A. Namely, the abutment A is engaged to the implant I based on a surface friction force between the well I2 and the post portion A3.

An expanding flare portion A4 is provided in an upper portion of the abutment A, and both sides of the same are cut into provide a conical head forming a slanted surface A5.

In the above conventional dental implant system, the engaging operation with respect to the alveolar bone S is implemented by the dental implant system I, and the abutment A supporting the crown C is engaged to the implant root I.

However, since an external force such as a uniting force is applied to the abutment A through the crown C, the strength of the above system is determined based an engaging force between the abutment A and implant root I and the strength of the implant root I itself.

When compared with the screw type of FIG. 1 in which the engagement is implemented based on the screw treads of screws A1 and A2 which have relatively smaller diameters, the locking taper method of FIG. 2 has much higher engaging forces, and it has a screw loosening problem. However, since the maximum strength is determined based on the minimum diameter of the engaging part, there is a big problem in that point.

Namely, when assembling the implant root I to the abutment A, the post portion A3 of the abutment A is inserted into the well I2 formed in the center of the implant root I. Therefore, the size "a" of the neck portion of the post portion A3 and the size "b" of the surrounding portion of the implant root I which size is obtained by subtracting the size of the neck portion are too small as shown in FIG. 3.

Therefore, a breaking problem may occur in case of the teeth requiring a larger uniting force such as back tooth,. The above problem may be most critical to the conventional implant system. So, it is most needed to overcome the above problem.

In particular, after being implanted, the minimum diameter of the surrounding cave of the implant is preferably about 2.0 mm. Therefore, in case of the constitution in FIG. 2, the minimum diameter should be 7.5 mm. The relatively small portion needs a small implant. The size of the neck portion of the post portion of FIG. 2 should be over 2.0 mm not to be easily broken. In the above conventional method, the actual use of the implant is limited due to the impossibility to decrease the size of the implant, In addition, if the size of the implant is much smaller, the implant may be easily broken. Therefore, there are many problems for actually using the same.

In the conventional implant of FIGS. 1 trough 3, the upper portion and lower portion of the implant root may not be formed at a certain angle therebetween.

Namely, when planting the implant root into the alveolar bone, it may be necessary to avoid an anatomical structure (cortex which forms a lower alveolar pipe, biperforate, and maxillary sinus) of a maxilla or mandible under a certain circumstance. In order to avoid the above anatomical structure, an implant root bent at a certain angle is necessary. However, since the conventional implant root has a well in the center of the same, it is impossible to form a bent type implant.

SUMMARY OF THE INVENTION

Accordingly, the present invention provides a dental implant system in order to overcomes the problems encountered in the conventional art.

It is an object of the present invention to provide a dental implant system which is capable of forming a post portion in an implant root and a well in an abutment as the locking taper method instead of a conventional art in which a well is formed in an implant root and a post portion is formed in an abutment, so that when engaging the same, it is possible to implement a stable engagement, fabricate a smaller size of the implant root, and plant the implant with avoiding an anatomical structure in the mouth.

To achieve the above object, In a dental implant system which includes an implant root 10 planted in an alveolar bone, an abutment 20 assembled to the implant root, and a crown 30 assembled to the abutment, the dental implant system in which:

the implant root 10 is formed in a cylindrical shape without a longitudinal well in the interior of the same, and comprises a circular rim groove 13 formed along an outer circumferential surface of an upper portion of the same, a post portion 11 having a first taper portion 14 and a second taper portion 15 below the circular rim groove 13, and a planting portion 12 and multiple protruded circular plate pins 12 below the post portion11; and the abutment 20 is formed in a cylindrical shape having an expanded portion 21 curved at middle of the same, and comprises a well 23 including a taper inner diameter potion 22 in the lower surface of the same, so that the post portion 11 of the implant 10 is inserted into the well 23, a crown engaging potion 25 including the expanded portion 21 in the upper side, and an engaging well 24 in an upper surface of the engaging portion; and the crown 30 is engaged to an upper side of the abutment and comprises an abutment post 31 corresponding to the engaging well 24 at a center portion of the interior of the crown.

BRIEF DESCRIPTION OF THE DRAWINGS

The present invention will become better understood with reference to the accompanying drawings which are given only by way of illustration and thus are not limitative of the present invention, wherein.

DESCRIPTIONS OF THE MAJOR ELEMENTS IN THE DRAWINGS

10: implant root
20: abutment
30: crown

DETAILED DESCRIPTION OF PREFFERED EMBODIMENTS

The preferred embodiments of the present invention will be described with reference to the accompanying drawings.

Figure 1:
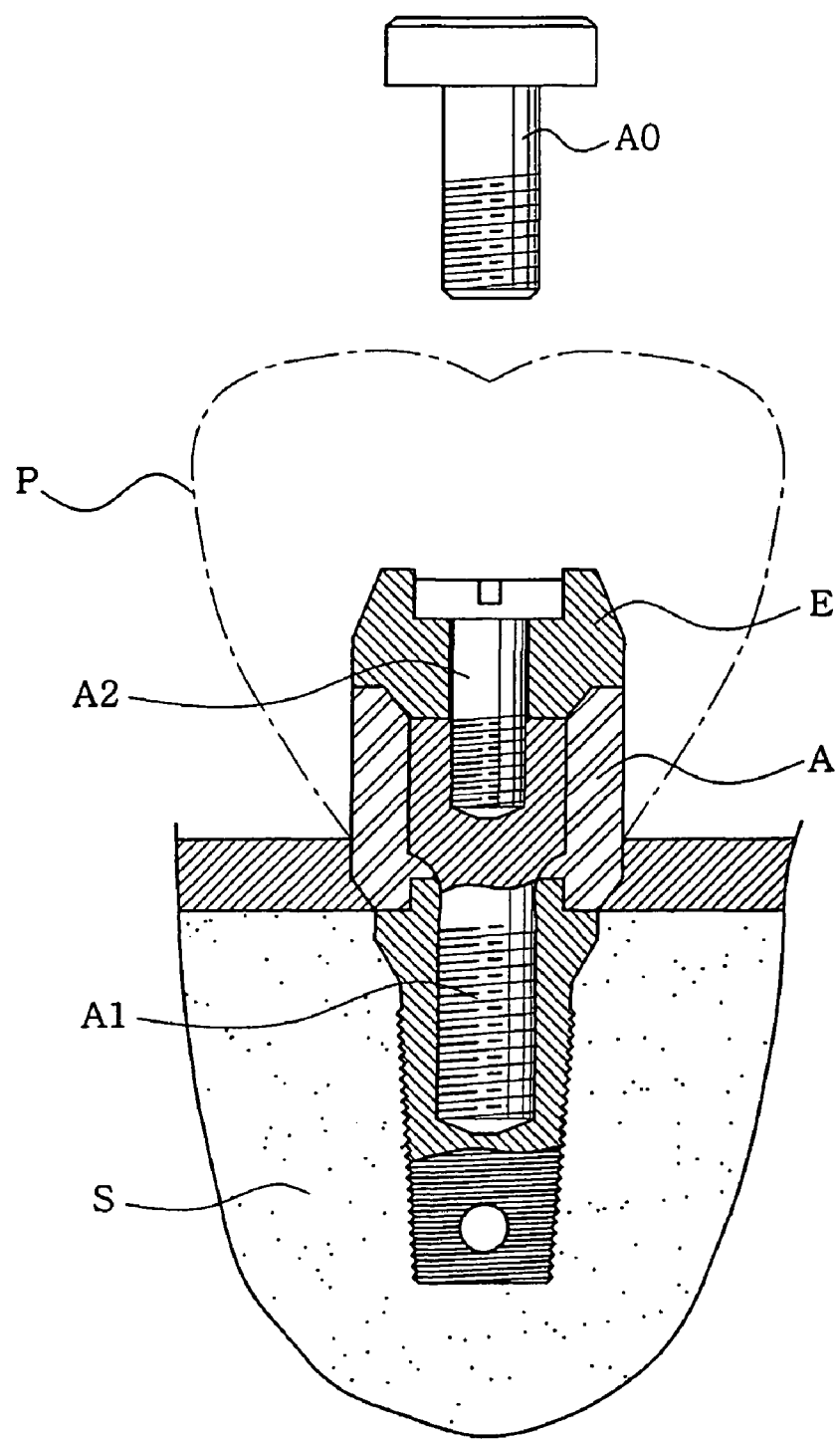
FIG. 1 is a cross-sectional view illustrating an example of an assembled state of a conventional dental implant system.
Figure 2:
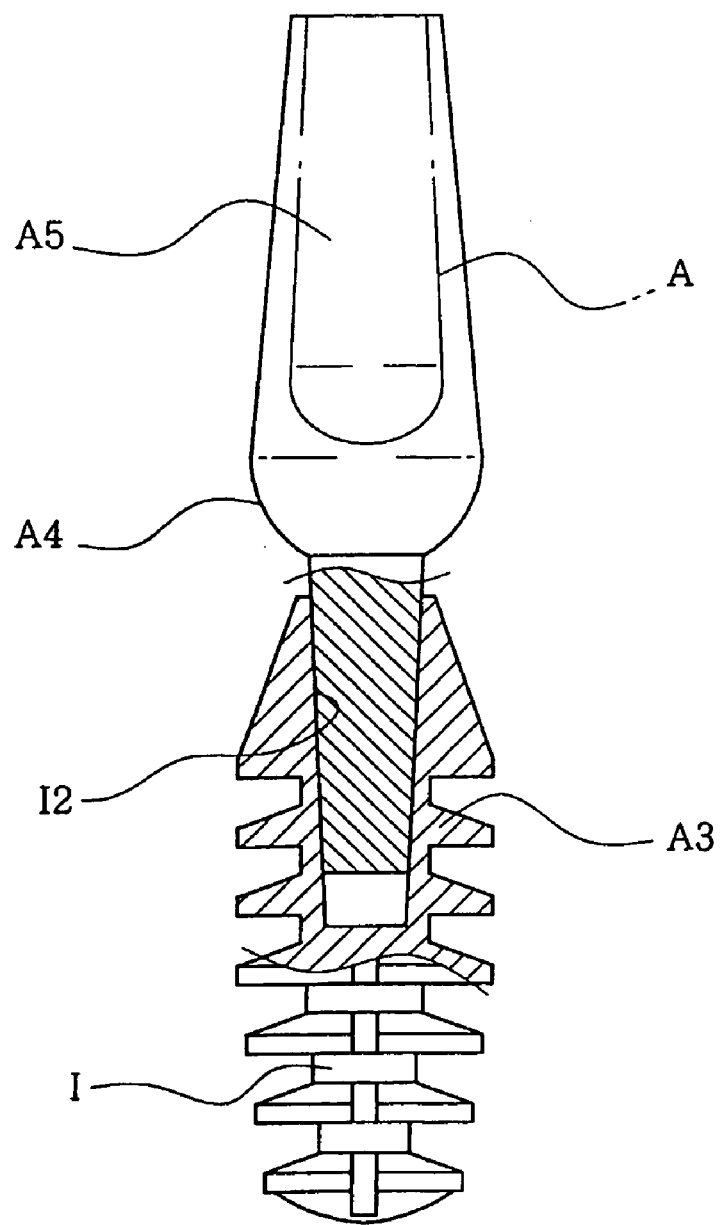
FIG. 2 is a cross-sectional view illustrating another example of an assembled state of a conventional tooth implant system.
Figure 3:
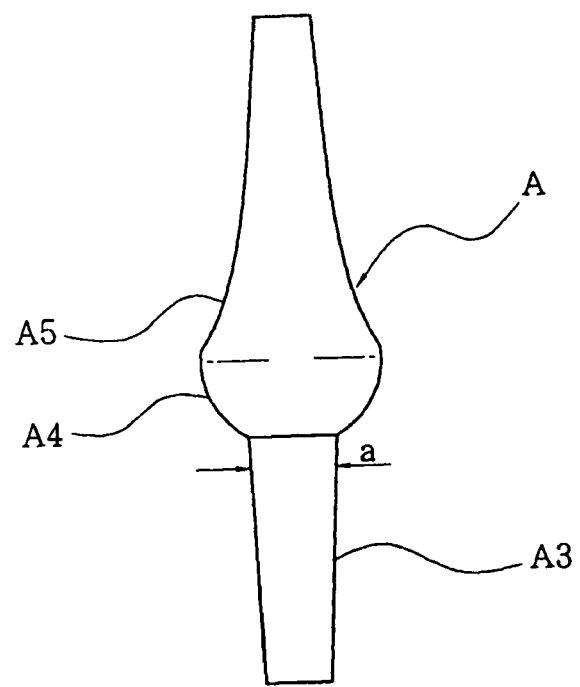
FIG. 3 is a disassembled cross-sectional view of FIG. 2.
Figure 3:
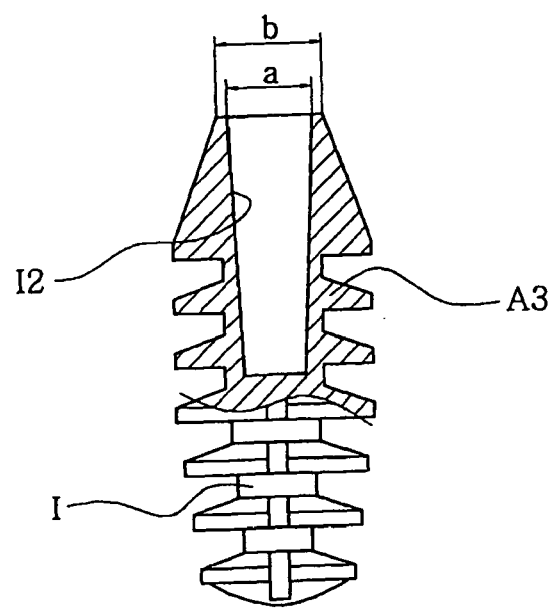
Figure 4:
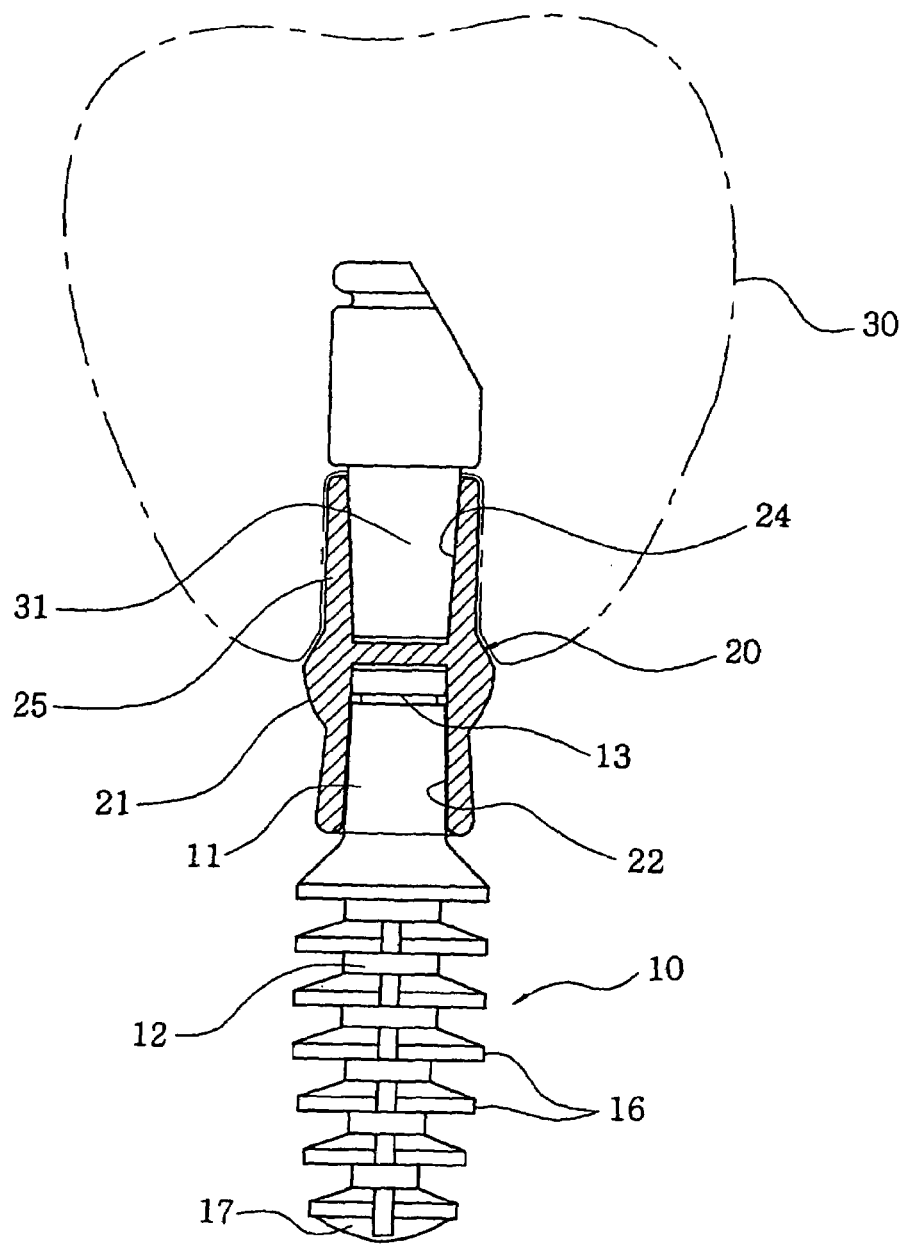
FIG. 4 is a cross-sectional view illustrating an assembled state of a dental implant system according to the present invention.
Figure 5:
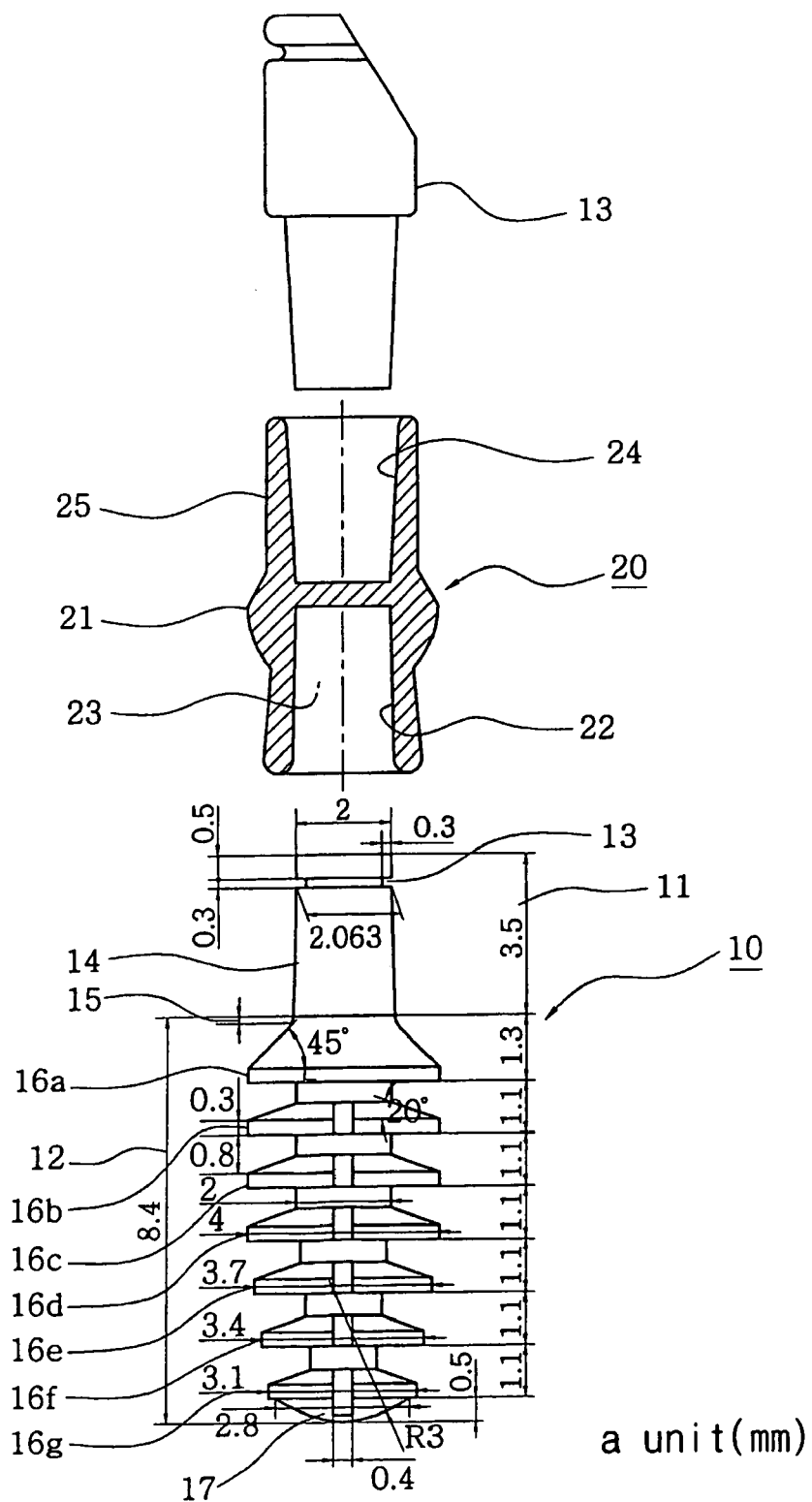
FIG. 5 is a cross-sectional view illustrating a disassembled state of a dental implant system according to the present invention.

FIG. 4 is a cross-sectional view illustrating an assembled state of an implant system according to the present invention, and FIG. 5 is a view illustrating a disassembled state of an implant according to the present invention.

As shown therein, the implant according to the present invention includes an implant root 10 and an abutment 20.

In a dental implant system which includes an implant root 10 planted in an alveolar bone, an abutment 20 assembled to the implant root, and a crown 30 assembled to the abutment, the dental implant system in which:

the implant root 10 is formed in a cylindrical shape without a longitudinal well in the interior of the same, and comprises a circular rim groove 13 formed along an outer circumferential surface of an upper portion of the same, a post portion 11 having a first taper portion 14 and a second taper portion 15 below the circular rim groove 13, and a planting portion 12 and multiple protruded circular plate pins 12 below the post portion11; and the abutment 20 is formed in a cylindrical shape having an expanded portion 21 curved at middle of the same, and comprises a well 23 including a taper inner diameter potion 22 in the lower surface of the same, so that the post portion 11 of the implant 10 is inserted into the well 23, a crown engaging potion 25 including the expanded portion 21 in the upper side, and an engaging well 24 in an upper surface of the engaging portion21.

FIG. 5 is a view illustrating an embodiment of the implant root 10 according to the present invention.

As shown in FIG. 5, in the implant root 10, the minimum diameter of the upper most portion of the post portion 11 is about 2 mm, and the height of the same is about 3.5 mm, and in the planting portion 12, the maximum diameter of the upper most circular plate pin 16 is about 4 mm, the height of the same is about 8 mm, and the call size of the same is 4*8.

There are about 7~8 call sizes from the relatively smaller sizes to the bigger sizes.

The circular rim groove 13 of the post portion 11 is formed in a portion lower from the upper surface by 0.5 mm, and has a width of about 0.3 mm and a depth of about 0.3 mm.

The circular rim groove 13 is adapted to prevent any escape of the implant due to a certain friction force when the abutment 20 is assembled.

The first taper portion 14 of the post portion 11 has a slant of about 1.5°. Namely, the diameter of the upper most portion in which the circular rim groove 13 is formed has the smallest size, and the size of the same is gradually increased torward the lower direction. When the minimum size of the upper most portion is about 2 mm, the diameter just before the second taper portion 15 is about 2.183 mm.

The second taper portion 15 has about 0.5 mm height from the first taper portion, and has a slant of about 3°, so that it is possible to implement a tight insertion when it is inserted into the well 23 of the abutment.

There are provided seven circular plate pins 16 of the planting portion 12. The first circular plate pin 16a of the upper most portion has a height of 1.3 mm, and a diameter of 4 mm, and the distance from the next second circular plate pin 16b to the seventh circular plate pin 16g is 1.1 mm.

In addition, the maximum diameters from the first circular plate pin 16a to the fourth circular plate pin 16d are same, and the diameters are gradually decreased in the directions of the fifth circular plate pin 16e through the seventh circular plate pin 16g in order for the teeth to have a natural physical appearance. The diameter of the seventh circular plate pin 16 of the lower most portion is about 3 mm.

The upper surface of the first circular plate pin 16a has a slant surface of about 45° in an opened umbrella shape, and the second circular plate pin 16b through the seventh circular plate pin 16g also have the opened umbrella shapes, and the upper surfaces of the same have a slant surface of about 20°.

In addition, a protrusion 17 is formed in a lower surface of the seventh circular plate pin 16g of the lower most portion. The protrusion 17 is adapted to eliminate an unnecessary alveolar bone removing work by coinciding an end blade portion of a reamer used for forming a well in the alveolar bone for the implant with the protrusion 17.

It is important to fabricate the implant root 10 according to the present invention in such a manner that the post portion 11 is slanted at a certain angle from the planting portion 12(in the conventional art, it is impossible to fabricate the implant bent at a certain angle due to a certain well in the interior of the same).

Figure 6:
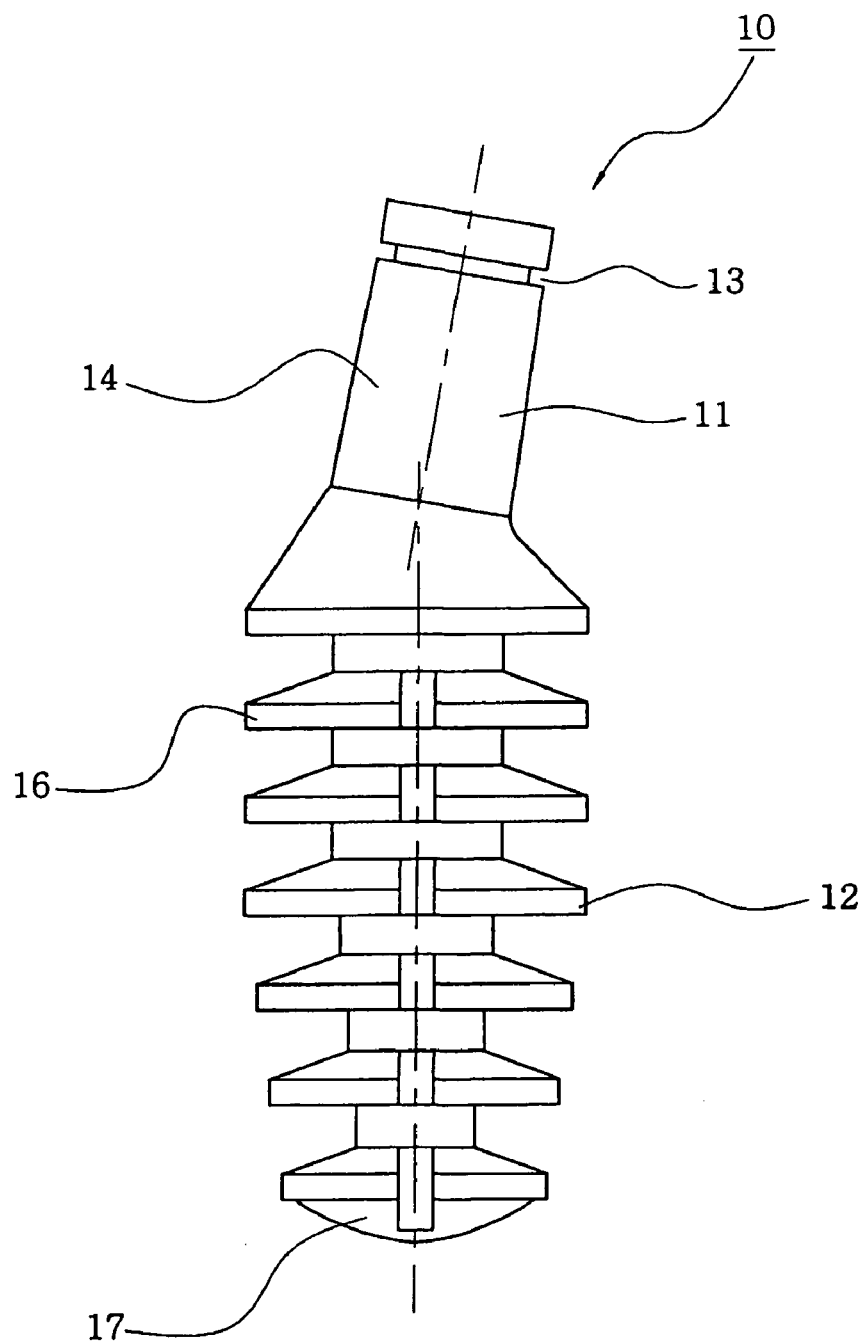
FIG. 6 is a view illustrating another embodiment of an implant according to the present invention.

The physical appearances of the post portion 11 and the planting portion 12 are the same as the above earlier embodiment of the present invention. As shown in FIG. 6, the post portion 11 is preferably slanted at about 10°~20° with respect to the planting portion 12.

In this case, even when the planting portion 12 is planted in a slanted state, the post portion 11 maintains a vertical state by avoiding the cortex bone formed of a lower alveolar pipe, biperforate, and maxilla in the major anatomical structure.

In addition, FIG. 5 is a view illustrating an embodiment of the abutment 20 according to the present invention, and there may be many abutments having different sizes and other physical appearances.

The abutment 20 is formed in a cylindrical shape having an expanded portion 21 curved at middle of the same, and comprises a well 23 including a taper inner diameter potion 22 in the lower surface of the same, so that the post portion 11 of the implant 10 is inserted into the well 23, a crown engaging potion 25 including the expanded portion 21 in the upper side, and an engaging well 24 in an upper surface of the engaging portion.

The taper angle of the inner diameter portion 22 into which the post portion 11 is inserted has an angle of about 1.5° in order for the abutment 20 to be used for the implant root 10.

The crown is engaged to the upper portion of the expanding portion 21, and an inner circumferential diameter portion of the well 23 is surface-processed for preventing any acid corrosion.

Therefore, when being engaged with the post portion of the implant, the lower most portion of the abutment is connected to the inner portion of the alveolar bone together with the post portion of the implant, so that it is possible to implement the maximum bone engagement thereby preventing an absorption of the alveolar bone.

When the well 23 formed in the lower portion of the abutment 20 is engaged with the post portion 11 of the implant root 10, the minimum diameter is the diameter of the lower portion of the abutment. Since this diameter is larger than that of the conventional abutment, it is possible to implement a better physical appearance when covering the crown.

For example, since in recovery of the front tooth portion of the maxilla, the thickness of the lower portion of the exposed portion in a natural tooth is more than about 7.0 mm, it is preferred that the thickness of the tooth diameter portions of the crown must be similar to the thickness of the lower portion of the exposed portion of the natural teeth after connecting the lower and upper implants in order to adapt a natural tooth shape. In the abutment according to the present invention, it is possible to implement a certain tooth diameter portion very similar to the natural teeth since the lower portion of the abutment is thicker than that of the conventional abutment.

Figure 7:
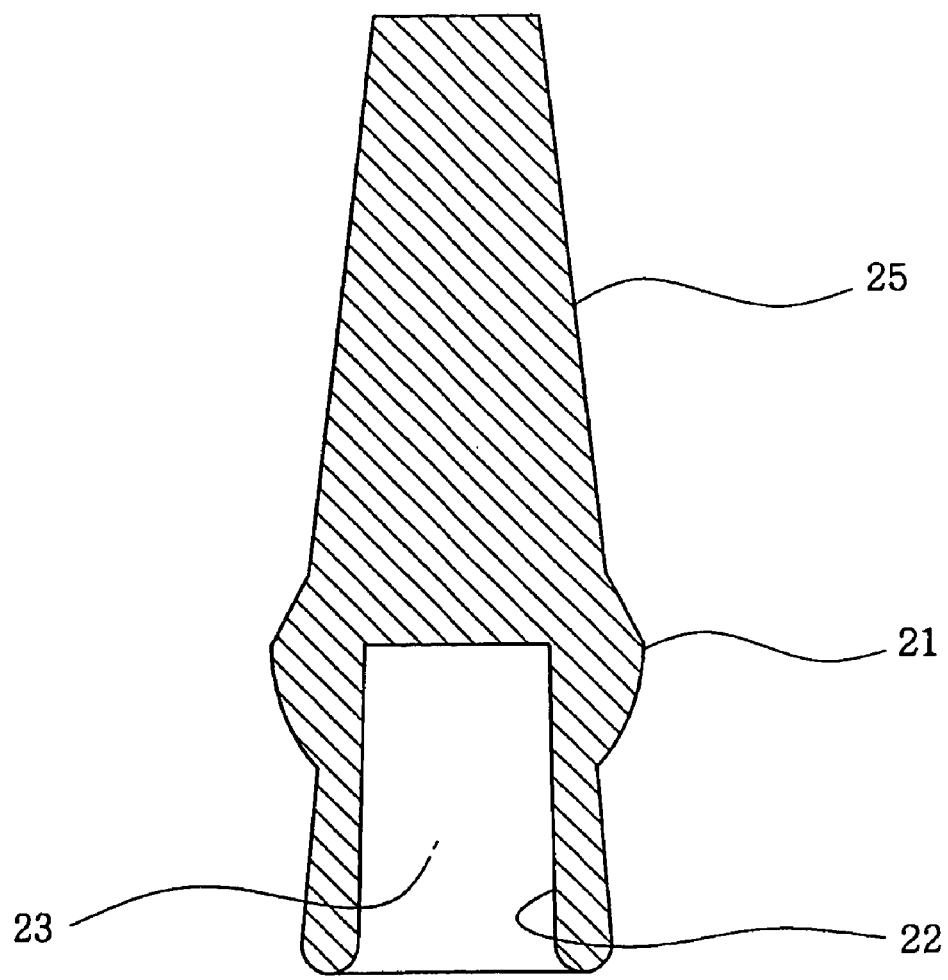
FIG. 7 is a view illustrating another embodiment of an abutment according to the present invention.

FIG. 7 is a view illustrating the abutment 20 according to the present invention.

As shown therein, an engaging well 24 is formed in an upper surface of the crown engaging portion 25 thereby implementing an easier engagement of the crown 30.

At this time, since the engaging well 24 is engaged according to the locking taper method, it is preferred to form a taper in the inner diameter portion having a slant of about 1.5°.

The post portion 31 of the abutment inserted into the engaging well 24 is adapted to engage the Resin crown for a path and synthetic resin of the crown. It is possible to prevent any escape of the crown based on the engaging well 24 without using a permanent cement. Therefore, in the present invention does not need to use a dental cement.

As described above, in the present invention, the post portion having the first taper portion and second taper portion is formed in the upper portion of the implant root compared to the conventional art in which the well is formed in the implant root, and the post portion is formed in the abutment. In addition, a well having a tapered inner diameter portion is formed in the lower surface of the abutment and implements a stable assembled state thereby providing an excellent support strength, decreasing the minimum diameter of the implant root, and bending the post portion at a certain angle with respect to the planting portion.

Since the abutment is assembled in such a manner that the outer diameter portion of the post portion is surrounded, the thickness of the tooth diameter portion is large, so that it is possible to implement a certain tooth diameter portion which is the same as the tooth diameter portion of the natural teeth. Furthermore, since an engaging well according to the locking taper method is provided for the engagement of the crown in the upper portion, it is possible to implement an easier assembling of the crown. Also, the present invention does not need to use the dental cement.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. In a dental implant system which includes an implant root to be implanted in an alveolar bone, an abutment assembled to the implant root, and a crown assembled to the abutment, the dental implant system in which:

the implant root is formed in a cylindrical shape without a longitudinal well in the interior of the same, and comprises a circular rim groove formed along an outer circumferential surface of an upper portion of the same, a post portion having a first taper portion and a second taper portion below the circular rim groove, and a planting portion and multiple protruded circular plate pins below the post portion; and the abutment is formed in a cylindrical shape having an expanded portion curved at middle of the same, and comprises a well including a taper inner diameter portion in the lower surface of the same, so that the post portion of the implant is inserted into the well, a crown engaging portion including the expanded portion in the upper side, and an engaging well in an upper surface of the engaging portion; and the crown is engaged to an upper side of the abutment and comprises an abutment post corresponding to the engaging well at a center portion of the interior of the crown.

2. The dental implant system of claim 1, wherein the first taper portion of the implant root and the taper inner diameter portion of the abutment have a taper having an angle of about 0.5°~2.5° with respect to a center line of the cylindrical shape.

3. The dental implant system of claim 1, wherein the center portion in the said post portion of the implant root is formed at an angle of about 10°~20° with respect to the center of the planting portion.

4. The dental implant system of claim 1, wherein the abutment includes an engaging well which engages the abutment post of the crown in the upper surface of the same.

5. The dental implant system of claim 4, wherein the engaging well of the abutment and the outer circumferential surface of the abutment post have a taper of an angle of about 0.5°~2.5° with respect to the center line of the cylindrical shape.

* * * * *